United States Patent [19]
Selman et al.

[11] Patent Number: 5,405,369
[45] Date of Patent: Apr. 11, 1995

[54] PHOTOCHEMICAL ABLATION OF GASTRO-INTESTINAL TISSUE FOR AUGMENTATION OF AN ORGAN

[75] Inventors: Steven H. Selman; Kenneth A. Kropp; Gregory D. Haselhuhn, all of Toledo, Ohio

[73] Assignee: Medical College of Ohio, Toledo, Ohio

[21] Appl. No.: 187,048

[22] Filed: Jan. 25, 1994

[51] Int. Cl.⁶ ............................................. A61B 17/00
[52] U.S. Cl. ................................... 607/88; 128/898; 604/20
[58] Field of Search ............................ 607/88–95, 607/40; 128/897–898; 606/2, 3, 13–16, 32–33; 604/20–21

[56] References Cited

U.S. PATENT DOCUMENTS

| | | | |
|---|---|---|---|
| 3,280,816 | 10/1966 | Priore | 607/88 X |
| 4,321,918 | 3/1982 | Clark, II | 607/88 X |
| 4,651,739 | 3/1987 | Oseroff et al. | 607/88 |
| 4,877,872 | 10/1989 | Morgan et al. | |
| 4,886,831 | 12/1989 | Morcos et al. | 607/88 X |
| 4,988,808 | 1/1991 | Morgan et al. | |
| 5,051,415 | 9/1991 | Morgan et al. | |
| 5,169,395 | 12/1992 | Narciso, Jr. | |
| 5,196,005 | 3/1993 | Doiron et al. | |
| 5,216,012 | 6/1993 | Morgan et al. | |
| 5,231,684 | 7/1993 | Narciso, Jr. et al. | |
| 5,354,293 | 10/1994 | Beyer et al. | 607/88 X |

*Primary Examiner*—Angela D. Sykes
*Attorney, Agent, or Firm*—Emch, Schaffer, Schaub & Porcello Co.

[57] ABSTRACT

The present invention provides a method for treating a human or animal patient amenable an organ augmentation with gastro-intestinal tissue which is, or will be surgically transplanted into the patient's organ. The gastro-intestinal tissue is sensitized with an effective amount of a photosensitive composition which accumulates in the gastro-intestinal tissue. The sensitized tissue is exposed to a source of electromagnetic radiation energy for a predetermined time, wavelength and intensity sufficient to cause cellular and/or mucosal tissue function of the sensitized tissue to diminish or cease.

27 Claims, 1 Drawing Sheet

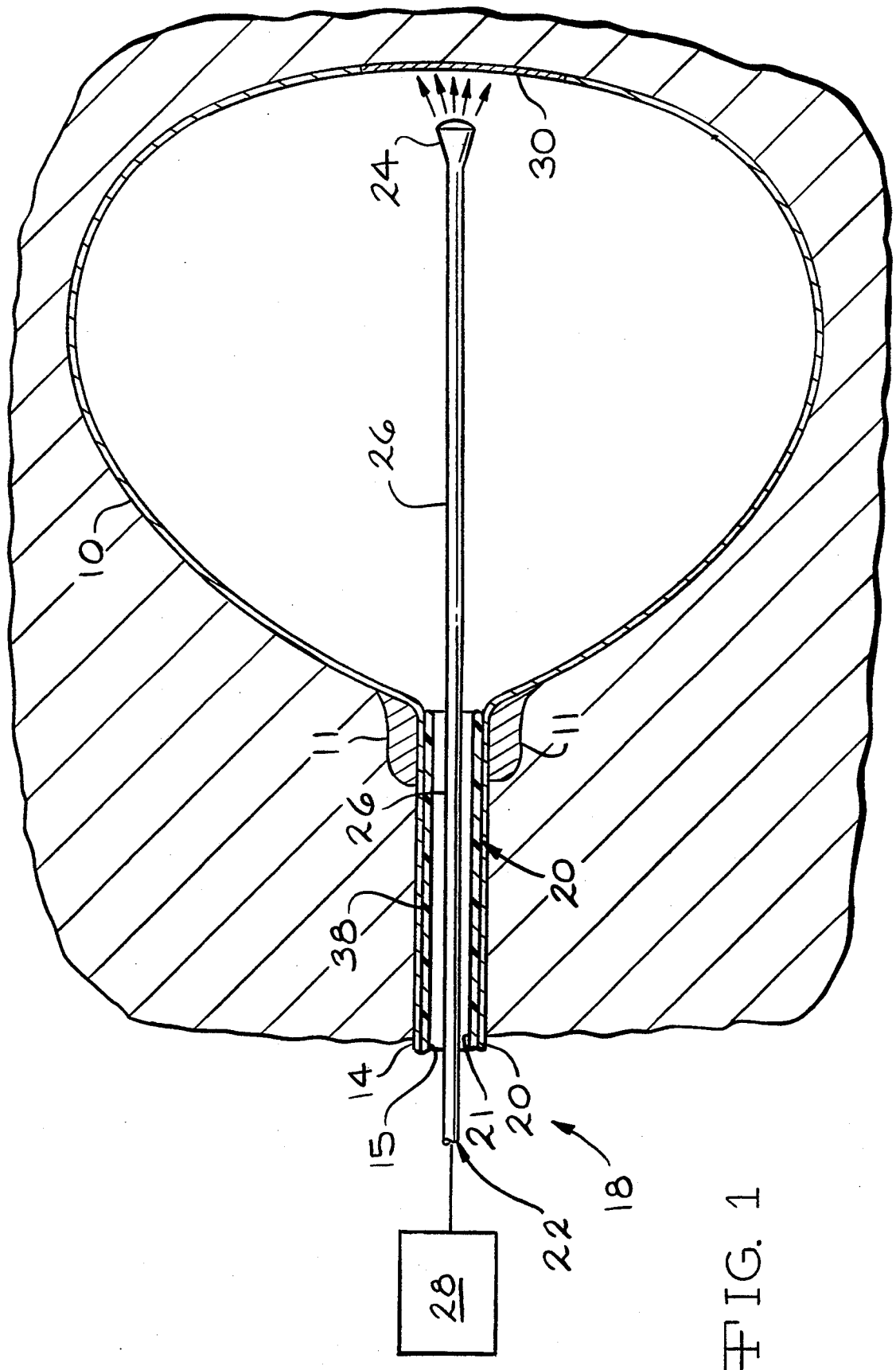

PHOTOCHEMICAL ABLATION OF GASTRO-INTESTINAL TISSUE FOR AUGMENTATION OF AN ORGAN

BACKGROUND OF THE INVENTION

This invention relates generally to the medical field and, more particularly, to the use of photodynamic therapy in organ augmentation, for example, enterocystoplasty or colocystoplasty or the use of other gasto-intestinal segments for organ augmentation. The present invention involves treatment of a patient using a photosensitive composition which selectively accumulates in mucosal tissues.

It is to be understood that the present invention is useful for augmentation of various organs. For ease of illustration, the specification herein describes in detail augmentation of a bladder organ using gastro-intestinal tissue. It is within the contemplated scope of the present invention that other organs using various tissues as augment are within the scope of the claimed invention.

The surgical treatment involved in augmentation of an organ involves exposing a portion of gastro-intestinal tissue (including stomach, large bowel (colon) and small intestine) and transplanting or inserting the exposed intestinal tissue into the organ. It is to be noted that various recipient organs such as the bladder, stomach and other portions of the gastro-intestinal tract, such as esophagus and the like, are contemplated as being within the scope of the present invention. In particular, bladder augmentation has been principally used in the treatment of patients with tuberculosis of the bladder, interstitial cystitis and bladder cancer. Currently, bladder augmentation is gaining wider acceptance as a therapeutic option for patients that have small, non-compliant bladders and for treating the variety of congenital, inflammatory and neoplastic problems in the urinary bladder which are refractory to medical management. Medical indications for bladder augmentation include fibrosed and scarred bladders from previous surgery, radiation therapy, or trauma; small non-compliant bladders associated with extrophy and epispadias; and, neurogenic bladders associated with myelodysplasia.

Despite significant advances in patient treatment using organ augmentation, there is a need for an improved augmentation procedure since numerous complications are associated with incorporating intestinal mucosa into the recipient organ. These complications include metabolic and electrolyte disturbances, such as hyperchloremic metabolic acidosis and hypokalemia; chronic bacterial colonization, which results in infections and/or sepsis; formation of stones or lithiasis; or malignant transformation at the vesicoenteric anastomosis. Still other complications arise from the fact that the intestinal mucosa continues to produce mucus after being transplanted into the recipient organ. The continued mucus production causes problems in patients. In bladder augmentation, for example, the continued mucus production requires frequent catheterization to prevent blockages in the genitourinary tract.

One attempt to overcome these complications involves mechanical stripping of the bowel mucosa layer while leaving the underlying submucosa and muscular layers intact. This mechanical stripping does lead to a decrease in mucus production. However, in the animal models tested, there is often marked retraction and fibrosis of the intestinal segment with little or no gain in organ capacity. The retraction and lack of increased organ capacity defeats the purpose of organ augmentation. Further, this type of mechanical surgical stripping of the mucosa is technically tedious and has limited potential application to humans.

Therefore, it is important that a method for organ augmentation include a way to decrease or prevent mucus production by the transplanted intestinal tissue while maintaining the elastic and muscular integrity of the transplanted tissue. The present invention addresses this problem.

In photodynamic therapy, photosensitive compositions are used to selectively diagnose, alter or destroy pathologic tissue. For example, photosensitive compounds are used which differentially localize in a target tumorous tissue where the compositions absorb electromagnetic radiation when irradiated. The photosensitive compositions are useful due to their ability to differentially localize in the target tissue as compared to the amount absorbed by the surrounding non-cancerous or normal tissues and produce toxic reactions when activated.

For example, photosensitive compositions have been proposed as useful compounds for topical applications for diagnosis and treatment of skin diseases. In addition, photosensitive compositions have been proposed for use to sterilize biological samples containing infectious agents such as bacteria and viruses. The bactericidal effects are induced by irradiation of tissues with photosensitive compositions against gram-negative and gram-positive microorganisms (Martinetto et al., Drugs Exp. Clin. Res. XII (4) 335–342, 1986). The photosensitive compositions have also been used to decontaminate blood and blood components. In addition, photosensitive compositions have been used in the treatment of blood vessel occlusions such as atherosclerotic plaques, thrombi and the like. Photodynamic therapy in combination with hyperthermia has also been proposed as a useful method in treating many of these disorders or diseases. Photosensitive compositions have also been proposed as useful in the diagnosis of disease. These photosensitive compositions have fluorescent properties and since the photosensitive compositions sequester in diseased tissues, fluorescent visualizations and/or measurement can be used to diagnose and localize the disease or to direct therapy to the affected tissues.

Until the present invention, there has been no suggestion of using photodynamic therapy in the in vivo treatment of benign protocol for patients who will benefit from intestinal mucosa transplanted into an organ.

DISCLOSURE OF THE INVENTION

The present invention provides a method of treating various organ disorders and in particular, for treating organ disorders amenable to such treatment as organ augmentation. The method of the present invention is less invasive than currently used methods of organ augmentation, requires less hospitalization, and avoids the possible complications which accompany other methods of organ augmentation.

According to the present invention, a photosensitive composition is administered to the patient which preferentially accumulates in gastro-intestinal tissue, which will or has been transplanted into a recipient organ. Electromagnetic radiation is applied to the tissue. The absorption of the electromagnetic radiation by the photosensitive composition damages or destroys the mucosal tissue cells without damaging the underlying submucosal or muscle layers of the transplant tissue. The transplant tissues maintain their desired elastic and strength properies. After damage or destruction of the bowel mucosal tissue cells, transitional epithelium cells migrate in from the surrounding tissue and repopulate or cover the transplant tissue segment. The migration of the epithelium cells of the organ obviates many of the problems normally associated with the retained transplant tissue within the organ, since there is a substantial decrease in both mucus production and in the absorption of fluid and chemicals from the recipient organ.

In one embodiment, the present invention is particularly useful in bladder augmentation (i.e. enterocystoplasty) procedures in which a patient's bladder is opened and a segment of the patient's gastro-intestinal tissue is attached to the bladder in order to increase the bladder capacity and/or repair damage to the bladder. This operation is used in patients with small contracted bladders, patients with bladder trauma or neoplasms. The lining of the transplanted tissue continues to secrete mucus and absorb fluid and chemicals from the urine. The method of the present invention cause the mucosal lining of the transplanted bowel tissue to diminish or cease mucus production without injuring or destroying the submucosal or muscular layers of the transplanted bowel tissue, thereby maintaining the transplanted tissue's elastic and strength properties.

BRIEF DESCRIPTION OF THE DRAWINGS

FIG. 1 is a simplified sectional view of a region of a patient showing a urethra and bladder, schematically illustrating one method of practicing the present invention.

DETAILED DESCRIPTION OF THE PREFERRED EMBODIMENT

According to the present invention, a photosensitive composition is administered to the patient. The photosensitive composition is preferentially retained or absorbed by gastro-intestinal (bowel) tissue and is sequestered in bowel tissue at a much higher level than in a recipient organ tissue. The photosensitive composition is taken up by various cells in the transplant segment of bowel. The transplant segment is exposed to electromagnetic radiation either before, during or after being transplanted into the recipient organ. The electromagnetic radiation is absorbed by the photosensitive composition and causes a series of chemical reactions which leads to damage or destruction of the mucosal layer of tissue of the transplant bowel segment, while sparing the submucosal and muscular layers of the transplant tissue. The structures of the recipient organ (i.e. the walls, blood vessels and muscle layers) are not damaged because the photosensitive composition does not accumulate in these structures in sufficient amounts to cause damage. The epithelial cells of the recipient organ grow in and cover the bowel submucosa and muscle such that there is little or no production of mucus by the transplant tissue.

The photosensitive composition can be administered pre-operatively, intraoperatively or post-operatively to the patient. It is also contemplated that the transplant tissue can be exposed to the electromagnetic radiation pre-operatively, intraoperatively or post-operatively after a period of pre-determined recovery period has passed. It is to be understood that the exact procedure of photosensitive composition administration and electromagnetic radiation treatment is dependent upon the individual parameters of each patient's situation and the localization properties of the photosensitive composition. It is to be understood that in various preferred embodiments, the organ augmentation will be performed followed by a suitable recovery period. Thereafter, at least one preferred photosensitive composition is administered to the patient. After a suitable period of time has elapsed in order preferentially allow the transplanted mucosal tissue to absorb and/or retain the photosensitive composition, electromagnetic radiation is administered to ablate the mucosal layer of the transplanted tissue. The photodynamic therapy damages or destroys the mucosa of the transplanted tissue, thereby allowing recovery of the submucosal layer of transplanted tissue with neothelium originating from the surrounding recipient organ tissue.

It is to be understood that in certain circumstances, exposing the intestinal segment to electromagnetic radiation intraoperatively may be difficult and it may be preferred to treat the patient after a post-operative period of convalescence. It is also contemplated that patients who have previously undergone organ augmentations and who are still experiencing continued mucus production and/or absorption of chemicals, can be treated with the method of the present invention. In such situations, the organ augmentation patients may receive the photosensitive composition and thereafter, receive the electromagnetic radiation treatment using a cystoscope to expose the intestinal augment to the electromagnetic radiation. The preferential retention of the photosensitive composition within the intestinal mucosa minimizes any possible damage to the underlying submucosa intestinal muscle of the transplant tissue to the surrounding recipient organ tissue. It is contemplated that this electromagnetic radiation therapy treatment can be performed as an outpatient under local or small amounts of IV sedation.

It is contemplated that various photosensitive compositions are useful in the present invention. There are various classes of useful photosensitive compositions, including, for example, porphyrins, chlorins (such as benzochlorins, benzochlorin metal complexes, bacteriochlorins and the like), purpurins, verdins, phthalocyanines and iminium salts of these compositions and other compositions. Various photosensitive compositions and include the use of tin ethyl eitopurpurin dichloride (SnET2), photorin, benzoporphyrin derivative, monaspartyl chlorin e6, and Zn-phthalcyanine. In addition, it is possible to use a photosensitive precursor, such as 5-aminolevulinic acid (ALA), which is a precursor to the production of the photosensitizer protoporphyin-IX in vivo. It is to be understood that the present invention envisions the use of these and other classes of photosensitive compositions, and the present invention is not limited to particular photosensitive compositions.

Examples of various known photosensitive compositions include those compounds disclosed in Loh et al., J. Photochem. Photobiol., 20:47–54 (1993), Selman et al., Photochem. Photobiol., 57:681–685 (1993), Morgan et al., J. Org. Chem. 51:1347–1350 (1986), Skalkos, et al., Med. Chem. Res. 2:276–281 (1992), the U.S. patent application Ser. No. 07/901,597 and Morgan, et al., U.S. Pat. Nos. 4,877,872, 4,988,808, 5,051,415 and 5,216,012 references, which are expressly incorporated herein. (All references disclosed herein form a part of the disclosure and are expressly incorporated by reference.) These compositions are physiologically acceptable for subcutaneous, intravenous, intravesical, or oral administration as solutions, emulsions or suspensions.

In addition to the required photosensitive composition, additional components may be chemically attached to or physically combined with the photosensitive composition for administration to the patient. These additional components may include labeling compositions, cytotoxins, immunoglobins, monoclonal antibodies and/or receptor ligands, which may enhance the photosensitive composition's selectivity for the desired tissue.

The photosensitive compositions and any additional components are formulated into a final pharmaceutical formulation for administration to the patient using techniques generally known in the art. The pharmaceutical formulation can be administered singly or as components of mixtures as solutions, emulsions or suspensions. It is to be understood that the final pharmaceutical formulations can be prepared in conventional forms either as liquid suspensions or solutions, solid forms suitable for solution or suspension and liquid prior to injection or as emulsions. The formulation may include suitable excipients such as saline, dextrose, glycerol, water and the like. The final pharmaceutical formulation may also contain additional components such as pH buffering agents, wetting or emulsifying agents and the like.

It is to be understood that the photosensitive compositions can be administered by any suitable route or method. These methods include, for example, subcutaneous, intravascular, intraperitoneal or intramuscular injection, oral or topical administration or a suppository administration. It is further contemplated that the photosensitive composition can be an extended release formulation, such that it is delivered over a period of time and there is a sustained release of the photosensitive composition. The extended release can be administered by a vascular stent or implantable device, or can be orally administered to a tablet or capsule, for example.

Various modes of administration are well known in the art and the administration can be implemented in a manner which is most suitable for delivery of the photosensitive composition. This administration can include a slower sustained release system or, if properly formulated, an oral administration. The quantity of the formulation being administered is dependent upon the choice of the active photosensitive composition, the condition to be treated, the mode of administration, the individual patient and the expertise and judgment of the practitioner. As such, smaller or larger doses may be needed depending upon the specificity of the formulation. It is contemplated that in formulations having such additional components such as highly specific monoclonal antibody preparations and specific receptor ligands, the dosages may be less than formulations which are less specific to the target tissue. It is contemplated that ranges in about 0.05–10 mg/kg are suitable. It is to be understood that these ranges are merely suggestive and many variables must be taken into consideration in the treatment of individual patients and variations from these recommended values are expected.

Other ingredients which can be included in the formulation include antimicrobial agents and/or preservatives as necessary. Many variations of the above, along with other suitable vehicles will suggest themselves to those skilled in the art in light of the description herein.

The photosensitive composition is administered in an effective amount such that a sufficient amount of the photosensitive composition accumulates in the desired target or transplant tissue. In certain embodiments of the present invention, a predetermined period of time is allowed to pass in order to optimize the accumulation and retension of the photosensitive composition in the target tissue. It is contemplated that various protocols of treatment using the method of the present invention may involve irradiating the photosensitive compositions after a suitable period of time has elapsed. It is contemplated that these time periods can range from a relatively short time of approximately one hour or less to a longer time of three to four days after administration of the photosensitive composition to the patient. However, it should be understood that the optimum time lapse (if any) between drug administration and irradiation depends on the type and amount of photosensitive composition administered, the patient's history and the judgment of the practitioner.

After the photosensitive composition accumulates in the transplant tissue, the tissue is irradiated with electromagnetic radiation of a predetermined wavelength and intensity at which the composition absorbs energy. This absorption of energy by the photosensitive composition causes a reaction which damages or destroys the desired cells or tissue in which the composition has accumulated.

It is to be understood that most photosensitive compositions both fluoresce and sensitize. Both fluorescence and sensitization are de-excitation pathways which are competitive to each other and are generally activated by any wavelength of electromagnetic radiation absorbed by the photosensitive composition, One wavelength does not excite only fluorescence while another wavelength causes the sensitization reaction.

It is contemplated that various types of electromagnetic radiation are useful with the present invention. Such electromagnetic radiation envisions the use of all the electromagnetic spectrum which is made up of photons. Useful electromagnetic radiation includes, for example, light in the ultraviolet, visible and infrared ranges and ultrasound. Such luminescence is dependent upon the photosensitive composition being used and the method of treatment. It is further to be understood that both the photosensitive composition and the electromagnetic radiation can be administered by any suitable method, These methods include both the in vivo and ex vivo administration of both the radiation and/or photosensitive composition. Further, the administration of both the drug and radiation therapy can be in a single application or if desired, multiple applications. Further, the sustained release administration of the photosenstive composition can be utilized to take advantage of the properties of the photosensitive composition and the electromagnetic radiation therapy treatment being administered.

It is to be understood that the particular wavelength and intensity of the electromagnetic radiation energy delivered to the tissue is dependent, in part, upon the type of photosensitive composition being used. In certain embodiments, photosensitive compositions which have absorbance peaks at shorter wavelengths and show greater absorbencies may be used. In various embodiments, the shorter wavelength peaks are advantageous because the light of the shorter wavelength is less capable of penetration into underlying tissue, while greater absorbencies in the photosensitive composition are desirable because less light energy is required to cause a given degree of reaction.

The wavelength of irradiating energy is chosen to match an absorbance peak of the photosensitive composition. The suitable wavelengths for the photosensitive compositions are readily determined by the composition's absorption spectrum. For example, in the deeper tissue penetration red wave length range of the visible electromagnetic radiation spectrum, the photosensitive composition tin ethyl etiopurpurin dichloride is illuminated with light that includes the absorption peak at about $665 +/- 5$ nm. 5-aminolevulinic acid is a precursor to protoporphyin-IX in vivo, which is the active photosensitive composition and which absorbs energy at about $630 +/- 5$ nm. The irradiation dosages are readily determined and dependent upon the method of delivery of the photosensitive composition and the type and amount of photosensitive composition being administered and retained by the target tissue. Thus, the intensities of light illumination will typically be in the range of more than about 5 to less than about 500 joules/cm$^2$ of light.

Irradiation of the target tissue containing the photosensitive composition in accordance with the instant invention can be achieved by delivering electromagnetic radiation energy from conventional light source, a laser, or by sending an electromagnetic signal from any other appropriate transmitting device. The particular method of irradiation of the tissue depends upon the location in the patient of the affected tissue.

It has been found that one particularly useful transmitting device comprises a laser which delivers highly accurate intensities and wavelengths of light through at least one optical fiber, For example, in one embodiment, the light energy is delivered through an optical fiber which can optionally have a light diffusing means operatively attached thereto. The light energy is delivered by placing the delivery means in a catheter. The delivery means is properly located and positioned adjacent the target tissue. A portion of the catheter is sufficiently transparent or translucent to allow the light energy to adequately irradiate the adjacent target tissue. The remaining catheter may be coated with an opaque or reflective shield type material such that light does not penetrate the adjacent muscle or recipient organ tissues, which is comprised of a diffusing material which allows the light to radiate from the optic fiber. For example, useful light sources are described in U.S. Pat. Nos. 5,169,395 and 5,196,005.

It is also contemplated that the electromagnetic radiation transmitting device can deliver using a spatially localized illuminator, such as a microlens fiber which provides a circular illumination field with good uniform density and sharp demarcation boundaries. For example, useful devices include U.S. Pat. No. 5,231,684.

The delivery means can be in the form of a light guide, such as a single optical fiber or a fiber optic bundle, which in preferred embodiments, comprises at least one optical fiber having an appropriate provision for lighting thereof. The delivery means and catheter each have a sufficiently small cross section so that the delivery means and catheter may be fabricated within the appropriate dimensions to comfortably fit within the patient's body or desired orifice. The catheter may be of a rigid type material or may be made of sufficiently flexible material for positioning the light delivery means and catheter throughout a tortuous path.

Also, it is contemplated that various other apparatuses may be employed within the scope of the present invention in order to ease the use of the method of the present invention by cleansing, heating and/or cooling the tissue being treated with the photodynamic therapy of the present invention. For example, when about 40°-45° C. heat is delivered to the tissue by, for example, microwave (not shown) or laser (not shown), the effects of the photodynamic therapy are enhanced.

It is also contemplated that the electromagnetic radiation can be provided with various means for guiding the delivery means through a lumen, and means for measuring light intensity, temperature and drug fluorescence or illumination. It is also contemplated that the delivery means can be provided with an irrigation apparatus to provide a source of irrigation to the area as desired and to keep the area being irradiated relatively clear.

Accurate positioning of the delivery means assures that there is limited penetration of electromagnetic radiation into the tissue and that only the desired tissue is irradiated. Such accurate positioning can be aided by using an ultrasound probe. It is also contemplated that other methods of accurately positioning the delivery means can be used. For example, the catheter and/or delivery means can have graduated marks thereon so that the actual position of the delivery means can be accurately located.

After proper localization of the delivery means is achieved, the transmitting device is operatively engaged and energy irradiates the adjacent target tissue. The preferred length of time of irradiation and wavelength of electromagnetic radiation are determined by the type and amount of photosensitive composition being used and other factors as described above. The irradiation of the photosensitive composition causes the photosensitive composition to absorb the electromagnetic radiation generally or induces a photochemical reaction of the photosensitive composition, thereby inducing damage or destruction of the desired tissue. The photosensitive composition may cause a hemorrhagic necrosis of the affected tissue. Further, with the passage of time there is subsequent diminishment or cessation of the cellular and/or tissue functions and subsequent atrophy of the affected tissue. For example, it is surprisingly found that in bladder augmentation procedures, the bladder tissue and the submucosa of the transplanted bowel tissue are spared any damage while the mucosal layer of the transplanted bowel tissue remains in the destroyed or atrophied state. The submucosal and muscular layers of the transplanted bowel tissue are repopulated with transitional epithelium that migrates in from the adjacent bladder tissue.

It is to be understood that various transmitting devices can be utilized in delivering the electromagnetic radiation to the desired target tissue. For ease of illustration of the present invention, the following description relates to photochemical ablation of gasto-intestinal mucosal tissue for a bladder augmentation. However, as described in detail above, various other organs are contemplated as being treated, along with other types of transplant tissue, as well as other types of electromagnetic radiation in addition to the ones described below.

Referring to FIG. 1, there is illustrated in simplified form a sectional view of a patient showing a bladder 10 (including the bladder sphincter muscle 11), and a urethra 14 in a distended condition and defining an opening or lumen 15.

A photodynamic therapy system or apparatus 18 generally comprises a catheter 20, a delivery means 22 and a source of electromagnetic radiation energy 28. The catheter 20 defines an opening 21 extending axially therethrough for receiving the delivery means 22. The delivery means 22 can comprise at least one, or alternately multiple, long, small diameter optic fibers. The delivery means 22 coaxially extends through the catheter 20. In a alternative embodiment (not shown), the delivery means 22 may be a part of the catheter 20. It is to be understood that the catheter 20 and the delivery means 22 may generally have a rounded or tapered configuration to minimize any damage to the urethral lining and to ease insertion of the catheter 20 and delivery means 22 into the opening 15 of the urethra 14 and into the bladder 10. At least a portion of the delivery means 22 is disposed within the bladder 10. The delivery means 22 has a directional distal end 24 (which is generally transparent or translucent) and a proximal end 26 which extends from the distal end 24 out of the patient's body to the electromagnetic radiation source 28 such as a laser, LED device, or lamp. The proximal end 26 of the delivery means 22 is preferably of an opaque and/or reflective material such that no light is delivered to any surrounding tissue.

The axial length of the distal end 24 is sufficient to generally illuminate an affected area 30, comprising the transplanted bowel tissue. In preferred embodiments, the length of the distal end 24 can vary depending upon the extent amount of light energy to be administered. It is understood that the preferable length of the distal end 24 will vary from patient to patient and that judgment of the practitioner will determine the proper length of the distal end 24 in order to accurately deliver the required light to the desired tissues. In certain embodiments, it is preferred that the distal end 24 be of a directional material, such that electromagnetic radiation, rather than radiating outwardly from the axis of the distal end into the tissues, is focused within well-defined boundaries. In the embodiment shown in FIG. 1, the affected area 30 receives the diffused light (schematically indicated with arrows). In other embodiments, it may be preferred that the distal end 24 be of a diffusing material such that the light radiates outwardly from the axis of the distal end 24 into the tissues.

It is contemplated that monitors (not shown) can be placed in the bladder 10 for measuring light intensity and temperature. This positioning of the catheter 20 and delivery means 22 can be aided using an ultrasound probe (not shown) and/or by direct visualization using an endoscope (not shown).

After the delivery means 22 is localized in the bladder 10, the energy source 28 is activated and energy is delivered to the affected tissue 30. The intensity, wavelength and duration of the energy are dependent upon many variables including the type and amount of photosensitive composition used. During this irradiation, it is possible to continuously monitor the position of the distal end 24 of the delivery means 22 such that there is little damage to the surrounding tissues. After irradiation, the catheter 20 and delivery means 22 are removed from the bladder 10 and urethra 14.

The following examples are intended to illustrate the present invention but not to limit its scope.

Example

33 Fischer 344 female exbreeder rats weighing between 200–250 grams were used. Eight (8) rats died in the immediate post-operative period (first 24 hours), secondary to either bleeding complications or anesthesia related causes. Of the remaining 25 rats, there were three control groups of five rats each and one treatment group consisting of ten rats. The treatment group was given five micrograms per kg of the photosensitizer hematoporphyrin derivative (HpD), intravenously 24 hours prior to bladder augmentation. At the time of surgery, approximately 1.5 cm's of terminal lieurn was isolated and used for ileocystoplasty. Primary anastomosis of the small bowel was performed using 7-O Vicryl suture in an interrupted fashion. The isolated segment of lieurn was opened along its antimesenteric border and aluminum foil was placed around this segment to protect the underlying tissues and roesenteric blood supply from the effects of the light. HpD has a peak absorption at about 630 nm. A diffuse non-coherent red light source was used to shine on the bowel mucosa for 20 minutes for a total delivered fluorescence of 240 $J/cm^2$. An infrared filter was used to limit the light spectrum to 590–750 nm. After this, the treated intestinal segment was used to perform the augmentation using the Goodwin cup-patch technique. 7-O Vicryl suture in running fashion was used to complete the anastomosis.

Each of the three control groups underwent bladder augmentation was well. One group had no further treatment, another group was given HpD only, and a third group was treated with light only. Each rat received 20,000 units/kg penicillin intramuscular prior to surgery. Post-operatively, the rats received 80,000 units PCN per 100 cc in their drinking water for one week. After this, the oral antibiotics were discontinued. Rompun (12 mg/kg) and ketamine (80 mg/kg) anesthesia were used.

Each rat underwent a pre-operative cystometrogram (CMG) to determine the bladder capacity prior to augmentation. A five french pediatric feeding tube was placed transurethrally into the bladder and the urine was removed. Next, saline was infused into the rat's bladder at a rate of 0.25 cc/minute. Bladder pressure were measured concomitantly. Bladder capacity was defined as the volume of saline required to achieve a pressure of 30 mm Hg (40 cm water) or the volume at which saline leaked around the feeding tube. The value selected was the one that occurred first.

Following a recovery period of six weeks, each rat was placed in a metabolic cage for 24 hours to collect urine to measure the amount of mucus production. The urine collected was cooled to four degree centigrade overnight, then centrifuged for three minutes. The urine was aspirated off and the remaining mucus was air dried. The amount of mucus production was quantified as the dry weight obtained.

Urine cultures were also obtained in each rat to check for evidence of factorial colonization. Rompun and ketamine anesthesia were used as described above. A small vertical suprapubic incision was made under sterile conditions to expose the bladder. Urine for culture was obtained by direct bladder aspiration in order to avoid contaminated specimens. The incision was closed with 4-O silk. Bacterial colonization was defined as greater than 100,000 organisms per cc.

After a period of at least 48 hours, a repeat CMG was performed to determine post-operative bladder capacity prior to euthanasia. This was done in the same fashion as described above. Next, a median sternotomy was performed and blood was obtained via direct cardiac aspiration for measurement to electrolytes (Na, K, Cl, and $CO_2$). Prior to euthanasia, 10% neutral buffered formalin was instilled into the bladder through a five french feeding tube and the bladder neck was tied off using 2-O silk. The bladder and augment were removed and placed within formalin to fix the tissues overnight. The next day, the bladders were opened to determine the presence of stone formation. Representative sections were obtained and submitted for histological preparation.

Histological examination of the bladders in all three control groups revealed an obvious transition zone between the native bladder and the augment. There was no evidence of transitional epithelium ingrowth from the bladder onto the surface of the augment. Alcian Blue and PAS stains confirmed the presence of mucin production within the small bowel mucosa. However, each of the treated bladders demonstrated ingrowth of transitional epithelium to completely cover the intestinal augment. The underlying intestinal muscular and serosal layers were left intact. In all but one case, there was no evidence of mucus producing epithelium using the special stains. In this instance, there were only two small foci of remaining mucin producing small bowel mucosa. There was also no evidence of fibrosis or collagen deposition in either the control or treated groups.

Since there was no difference histologically between any of the control groups, the data obtained from each one was combined for comparison with the treatment group. In order to confirm the histological findings, urine collections were performed to measure the amount of mucus excreted in a 24 hour time period. The treated rats produced significantly less mucus than the control rats. The mean amount of mucus excreted by the controls (n=15) was 18.9 micrograms over 24 hours. The treated rats (n=10) produced only 5.7 micrograms of mucus. The treated rats also had a lower incidence of factorial colonization when compared to the controls. Two controls had significant bacteria counts in their urine while none of the treated animals did. No difference was seen in the electrolyte values between both groups. Two treated rats developed stones whereas none of the control rats did. This is presumably secondary to the fact that when the intestinal mucosa sloughs off after photodynamic therapy, the suture used to make the anastomosis is exposed to the urine. This can be obviated by using a suture like chromic with a shorter half life and by allowing a two to four week recovery period after bladder augmentation. After this, a light source can be passed transurethrally to perform the treatment. Lastly, the bladder capacity in all groups increased after bladder augmentation. The mean pre and post-operative bladder capacities in the control rats were 0.89 cc and 1.97 cc pre and post-operatively. The larger post-operative bladder capacity in the control rats can be explained by the fact that large amount of mucus were found in these bladders at the time of fixation. This mucus created a functional bladder outlet obstruction with poor emptying of the bladder and therefore a larger capacity.

It will be appreciated by a person of ordinary skill in the art that while the present invention has been disclosed and described herein with respect to certain preferred embodiments and alternatives thereof, various changes in form and detail may be made therein without departing from the scope and spirit thereof.

We claim:

1. A method for treating a human or animal patient amenable to an organ augmentation procedure, wherein gastro-intestinal tissue is surgically transplanted into the patient's organ, which method comprises sensitizing the gastro-intestinal tissue with an effective amount of a photosensitive composition which accumulates in the gastro-intestinal tissue and exposing the gastro-intestinal tissue to a source of electromagnetic radiation energy for a predetermined period of time and at a predetermined wavelength and intensity, whereby the photosensitive composition accumulated in the irradiated-exposed gastro-intestinal tissue absorbs the electromagnetic radiation or undergoes a photochemical reaction.

2. The method of claim 1, in which the electromagnetic radiation energy causes cellular and/or mucosal tissue function of the transplant intestinal tissue to diminish or cease.

3. The method of claim 1, in which the gastro-intestinal tissue is sensitized with the photosensitive composition prior to the transplantation of the gastro-intestinal tissue into the patient's organ.

4. The method of claim 1, in which the gastro-intestinal tissue is sensitized with the photosensitive composition during the transplantation of the gastro-intestinal tissue into the patient's organ.

5. The method of claim 1, in which the gastro-intestinal tissue is sensitized with the photosensitive composition after the transplantation of the gastro-intestinal tissue into the patient's organ.

6. The method of claim 1, in which the organ receiving the gastro-intestinal tissue is the patient's bladder.

7. The method of claim 1, in which the electromagnetic radiation energy comprises ultraviolet light, visible light, infrared light or ultrasound.

8. The method of claim 1, in which the gastro-intestinal tissue is sensitized by administering the photosensitive composition to the patient by injection, topical, oral or suppository administration.

9. The method of claim 1, in which the photosensitive composition is administered to the patient in an amount of about 0.05–10.0 mg/kg of the patient's weight.

10. The method of claim 1, in which an electromagnetic delivery means having a directional distal end is positioned adjacent or within the patient's sensitized gastro-intestinal tissue prior for delivery of the electromagnetic radiation energy to the sensitized gastro-intestinal tissue.

11. The method of claim 1, wherein the electromagnetic radiation delivery means comprises an optical fiber which directs light within defined boundaries.

12. The method of claim 1, wherein the electromagnetic radiation delivery means comprises an optical fiber which radially diffuses light.

13. The method of claim 1, which further includes treating the sensitized tissue with hyperthermic therapy.

14. The method of claim 1, in which the photosensitive composition comprises photofrin, protoporphyrin-IX, tin ethyl etiopurpurin dichloride or hematoporphyrin derivative.

15. A method of treating a patient who will have, is having or has had an organ augmentation with gastro-intestinal tissue comprising the steps of:
(a) providing an apparatus for diagnosing or treating tissue comprising:
a catheter for insertion into the patient's organ, the catheter having a proximal end and a distal end;
the catheter comprising at least one axially extending opening therethrough for receiving an electromagnetic radiation delivery means;
the delivery means having a transparent or translucent distal end and an opaque and/or reflective proximal end;

the delivery means being operatively connected to a source of energy for delivery of electromagnetic radiation to the distal end of the delivery means;

b) determining the position of the delivery means relative to the gasto-intestinal tissue and surrounding tissue of the patient to ensure that the distal end of the delivery means is adjacent the gastro-intestinal tissue;

c) administering to the patient an effective amount of a photosensitive composition at a point in time prior to or during irradiation of the gastro-intestinal tissue; and d) irradiating the gastro-intestinal tissue by delivering electromagnetic radiation energy through the distal end of the delivery means to the gastro-intestinal tissue; the energy being delivered for a predetermined time and at a predetermined wavelength and intensity sufficient to effectively treat the gastro-intestinal tissue.

16. The method of claim 15, in which the electromagnetic radiation energy causes cellular and/or mucosal tissue function of the transplant intestinal tissue to diminish or cease.

17. The method of claim 15, in which the gastro-intestinal tissue is sensitized with the photosensitive composition prior to the transplantation of the gastro-intestinal tissue into the patient's organ.

18. The method of claim 15, in which the gastro-intestinal tissue is sensitized with the photosensitive composition during the transplantation of the gastro-intestinal tissue into the patient's organ.

19. The method of claim 15, in which the gastro-intestinal tissue is sensitized with the photosensitive composition after the transplantation of the gastro-intestinal tissue into the patient's organ.

20. The method of claim 15, in which the organ receiving the gastro-intestinal tissue is the patient's bladder.

21. The method of claim 15, in which the electromagnetic radiation energy comprises ultraviolet light, visible light, infrared light or ultrasound.

22. The method of claim 15, in which the gastro-intestinal tissue is sensitized by administering the photosensitive composition to the patient by injection, topical, oral or suppository administration.

23. The method of claim 15, in which the photosensitive composition is administered to the patient in an amount of about 0.05–10.0 mg/kg of the patient's weight.

24. The method of claim 15, wherein the electromagnetic radiation delivery means comprises an optical fiber which directs light within defined boundaries.

25. The method of claim 15, wherein the electromagnetic radiation delivery means comprises an optical fiber which radially diffuses light.

26. The method of claim 15, which further includes treating the sensitized tissue with hyperthermic therapy.

27. The method of claim 15, in which the photosensitive composition comprises photofrin, protoporphyrin-IX, tin ethyl etiopurpurin dichloride or hematoporphyrin derivative.

* * * * *